United States Patent [19]

Hiejima et al.

[11] Patent Number: 5,531,688

[45] Date of Patent: Jul. 2, 1996

[54] APPARATUS FOR DOSING A LIQUID MEDICINE

[75] Inventors: Katsuhiro Hiejima, Ootsu; Hidekazu Miyauchi, Kusatsu, both of Japan

[73] Assignee: Nissho Corporation, Osaka, Japan

[21] Appl. No.: 523,629

[22] Filed: Sep. 5, 1995

[30] Foreign Application Priority Data

Sep. 2, 1994 [JP] Japan .................................. 6-209628

[51] Int. Cl.⁶ .................................................. A61M 5/00
[52] U.S. Cl. .......................... 604/96; 604/132; 604/246
[58] Field of Search ............................ 604/132, 212, 604/213, 246, 247, 131, 96

[56] References Cited

U.S. PATENT DOCUMENTS

| | | | |
|---|---|---|---|
| 4,140,117 | 2/1979 | Buckles et al. | |
| 4,386,929 | 6/1983 | Peery et al. | 604/132 |
| 4,909,790 | 3/1990 | Tsujikawa et al. | 604/132 |
| 4,915,693 | 4/1990 | Hessel | 604/132 |
| 5,080,652 | 1/1992 | Sancoff et al. | 604/132 |
| 5,120,315 | 6/1992 | Hessel | 604/132 |
| 5,178,610 | 1/1993 | Tsujikawa et al. | 604/132 |
| 5,211,632 | 5/1993 | Tsukada | 604/132 |

FOREIGN PATENT DOCUMENTS

0452912A2  10/1991  European Pat. Off.

*Primary Examiner*—John D. Yasko
*Attorney, Agent, or Firm*—Ronald J. Kubovcik

[57] ABSTRACT

An apparatus for dosing a liquid medicine has a balloon (1), a housing (3) and a delivery assembly 'b'. The balloon receives and discharges a liquid medicine under pressure. The housing enclosing the balloon has an opening communicating with the assembly 'b' in which a flow regulator (10) is installed. The balloon (1) is composed of flat and expansible sheets secured to both side rims of a short cylindrical frame (2). The flat sheets constituting the balloon are of an even thickness over their whole area, even after being inflated with the medicine, so that the pressure as well as the flow rate of the medicine effluent from the balloon will scarcely vary at the mouth over the course of time. Thus, the liquid medicine is dosed to a patient at a constant flow rate through the regulator.

7 Claims, 9 Drawing Sheets

APPARATUS FOR DOSING A LIQUID MEDICINE

BACKGROUND OF THE INVENTION

1. Field of the Invention

The present invention relates to an apparatus for continuously dosing a patient with a liquid medicine at a moderate rate, by feeding it into a vein, urinary cyst or like organ. More particularly, the present invention relates to an apparatus that comprises a balloon accommodating a compressed amount of a liquid medicine to be supplied to a patient at a constant and moderate rate and in a continuous manner.

2. Prior Art

A device of a certain type for continuously dosing a patient with an antibiotic, anti-cancer medicine or the like is disclosed in Japanese Unexamined) Patent Publication Sho. 50-108970. This device comprises an elastic balloon which holds the medicine and tends to shrink to squeeze it into the patient's body. A bladder for a liquid medicine dispenser is proposed in Japanese Patent Publication Sho. 59-48881. The bladder is made of a synthetic polyisoprene. One of the present inventors a few years ago proposed an improved balloon for use in a device to continuously and constantly exert pressure on a liquid medicine. This balloon is a length of natural rubber tube having its inner surface coated with a silicone resin membrane, and has a composite structure in cross section as shown in Japanese Unexamined Patent Publication Hei. 4-2360.

Since the prior art balloons are cylinders having either or both ends closed, it has been difficult to manufacture a balloon having a peripheral wall of uniform thickness. Cylindrical balloons of an uneven wall thickness are likely to assume an irregular shape when inflated with a liquid medicine, due to an uneven distribution of stress. Consequently the flow rate of liquid medicine effluent through an outlet of the balloons has been observed to vary in the course of time. This in turn causes a fluctuation in pressure at an inlet of a flow regulator and a failure to dose the medicine at a constant rate to a patient and, thus, a failure to meet a requirement of the present invention.

SUMMARY OF THE INVENTION

Researches made by the present inventors in an effort to overcome such a drawback in prior art balloons has lead to the present invention. The present invention is based on the finding that any uneven wall thickness of balloons inflated with a liquid medicine is likely to cause an unstable dosing rate. The present invention provides a novel apparatus for dosing a liquid medicine, the apparatus consisting of a balloon assembly and a delivery assembly connected thereto, the balloon assembly comprising: flat and flexible sheet-shaped balloon members inflatable to define therebetween an inside space for accommodating an amount of a liquid medicine in a compressed state; a housing for enclosing the balloon members in an inflated state thereof; and a short cylindrical frame intervening the balloon members and having a narrow peripheral wall in which a primary mouth is formed to be directly or indirectly in fluid communication with the inside space, and the delivery assembly extending outwardly from the primary mouth so as to discharge the medicine out of the balloon assembly, wherein circular edges of the flat and flexible balloon members are secured to both side rims of the cylindrical frame so as to assume a drum as a whole.

The apparatus provided herein utilizes the compression of a balloon inflated with a liquid medicine dose the same to a patient, as in the usual apparatus of this type. The liquid medicine effluent from the balloon will flow through a tubing having a flow regulator. This regulator will control the flow rate of the medicine before the medicine is injected into the patient through an injection needle connected to a distal end of the tubing. The balloon will previously be charged with the medicine by using a syringe filled therewith, wherein an end of the syringe will be inserted into the mouth located adjacent to and in fluid communication with the opening of the balloon. The flat sheets constituting the balloon are of an even thickness over their whole area, even after being inflated with the medicine. Therefore, the pressure as well as the flow rate of the liquid medicine effluent form the balloon will scarcely vary at the opening thereof over the course of time. The flow regulator which receives such a stable flow of medicine can thus does it to a patient at a constant flow rate.

THE PREFERRED EMBODIMENTS

Figure 1:
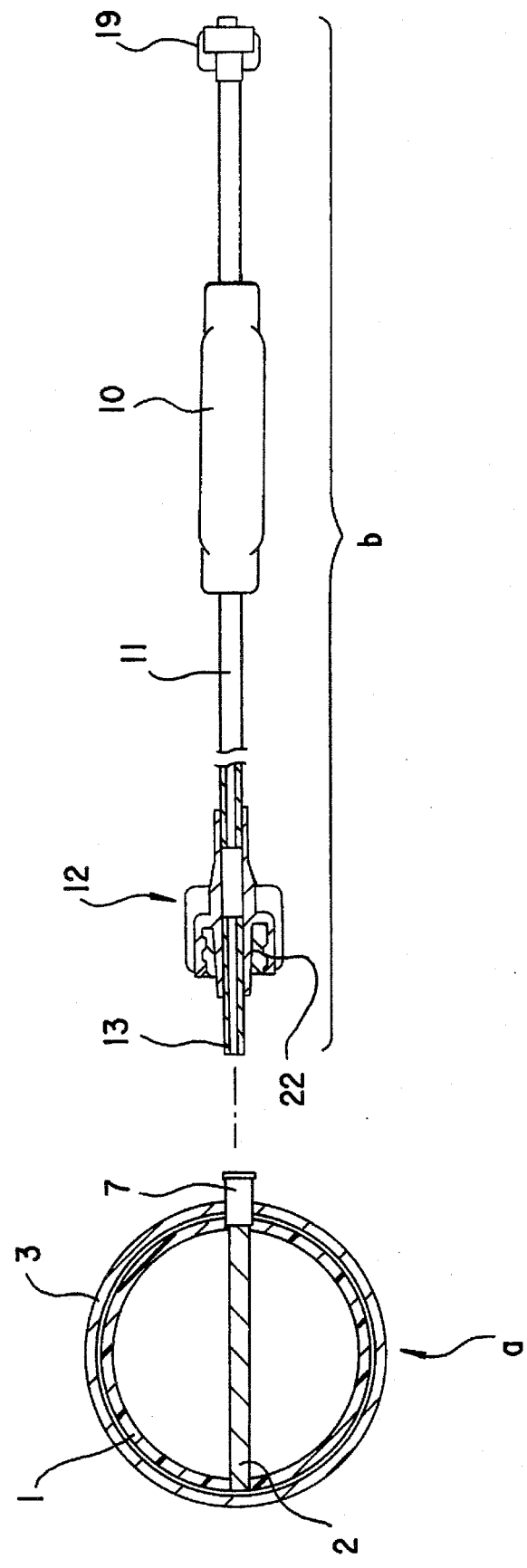
FIG. 1 is a cross-sectional view of an apparatus of the present invention for dosing a liquid medicine, the apparatus being provided in a first embodiment having a balloon filed with the medicine and ready for connection with a delivery assembly.

The present invention will now be described in more detail with reference to the drawings. In a first embodiment shown in FIG. 1, an apparatus for dosing a liquid medicine is composed of a balloon assembly 'a' for holding a liquid medicine and a delivery assembly 'b' for supplying the medicine. The balloon assembly may be set in place anywhere in proximity to a human body to be dosed with the liquid medicine. The assembly 'a' comprises sheet-shaped balloon members 1 and 1' which have circular edges secured to both side rims of a short (almost ring-shaped) cylindrical frame 2. The balloon 1 inflatable with the medicine as illustrated in FIG. 1 is connected by a lockable adapter 7 to delivery assembly 'b'. In use, the liquid medicine will flow out of the balloon assembly, through a tubing 11, a flow regulator 10, a distal connector 19 and an injection needle (not shown) for pricking the skin of a human. The balloon assembly 'a' has a hydrophobic filter (not shown in FIG. 1) which can be located opposite the lockable adapter 7. Air and gases can pass through this filter, but liquids are prevented from doing so.

Figure 2:
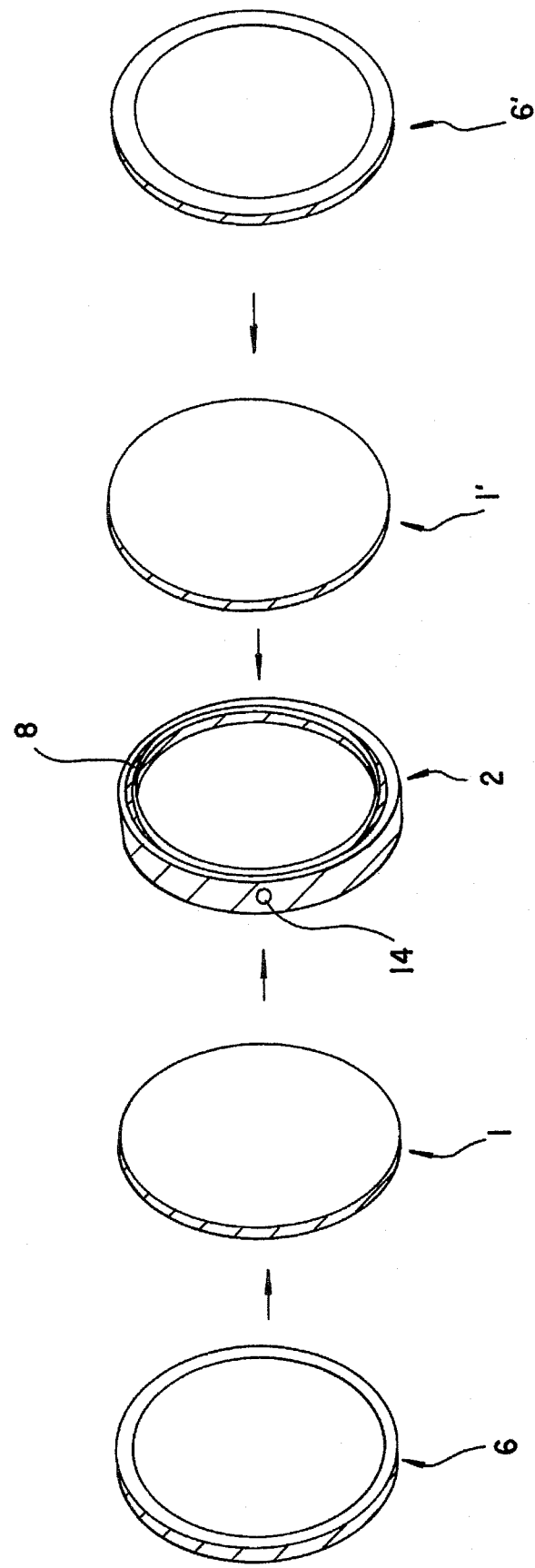
FIG. 2 is a perspective view of a process for manufacturing the balloon shown in FIG. 1.
Figure 3:
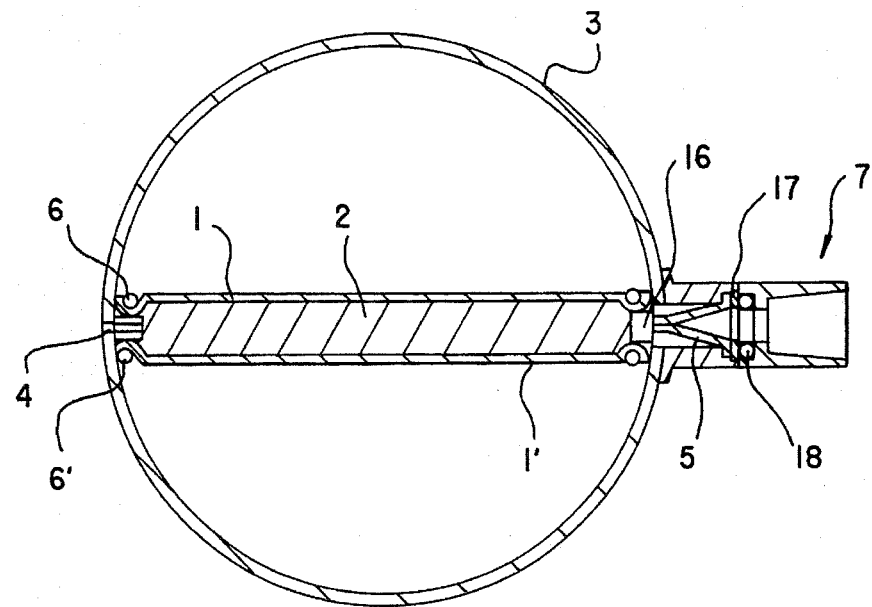
FIG. 3 is a cross-section of the balloon assembly shown in FIG. 1.

The sheet-shaped balloon member 1 and 1' secured to respective side rims of short cylindrical frame 2 assume a 'drum' shape as a whole. FIG. 2 shows the process of manufacturing the balloon assembly 'a'. First, the balloon members 1 and 1' are placed on respective sides of said frame 2, in such a manner that circular grooves 8 formed in said sides are covered and closed with the circular edges of those members. Subsequently, fasteners 6 and 6' each resembling an O-ring are pressed in the annular grooves 8, as seen in FIG. 3. The sheet-shaped balloon members 1 and 1' are fixed by the fasteners 6 to both the sides of the short cylindrical frame 2 having a narrow inside space. The hydrophobic filter 4 is located diametrically opposite to a mouth 16 which is formed in a narrow peripheral wall of said frame 2 so as to allow the liquid medicine to enter or leave the space. The gas-permeating filter 4 may be made of a polyester fabric, a fluoroplastic sheet or a laminate of the polyester fabric and the fluoroplastic sheet. The air remaining between the sheet-shaped balloon members 1 and 1' will be purged through the hydrophobic filter 4, when a liquid medicine is supplied to the balloon assembly.

The balloon assembly composed of members 1 and 1' will substantially assume a sphere as a whole if and when inflated with the medicine. The balloon members need not be of any specified size or thickness in the invention, since they should vary depending on the quantity of medicine to be dosed and the rate of dosing the same to a patient. The material of balloon members 1 and 1' must be such that the liquid medicine introduced into the inside space causes them to expand, while they tend to shrink to exert pressure on the medicine. Examples of the material include: an elastomer or a natural rubber such as silicone rubber, butyl rubber, acrylonitrile-butadiene rubber, butadiene rubber, isoprene rubber, polyurethane rubber, styrene-butadiene rubber, perprene, Clayton rubber and the like; any mixture thereof; and any laminated sheet composed of these rubbers. If a laminate is used to form the balloon members, an outer layer of the laminate is preferably made of the elastic material exemplified above, with an inner layer being made of any other rubber or thermoplastic resin which has a lower shrinkage stress. Examples of the thermoplastics include: an undrawn film, a monoaxially-drawn film and a biaxially-drawn film of polyethylene, polypropylene, polyvinyl chloride, polyester or polyamide.

A mouth 16 formed through a small cylindrical attachment is aligned with an opening 14 penetrating the narrow peripheral wall of the cylindrical frame 2, as shown in FIGS. 2 and 3. This attachment has a basal end secured to an outer surface of a housing 3. The housing will protect the balloon members 1 and 1' from puncture and breakage due to collision with an acute object, and will also inhibit liquid medicine from being ejected through a possible pin hole of said members. An opening (not shown) for ventilation is formed through a proper portion of the housing 3. Air and gases can pass through a hydrophobic filter attached to this opening, but liquids are prevented from doing so.

Installed in the mouth 16 are a check valve 5 of the duckbill type, a fixed disc 17 and a seal 18 arranged in this order away from the balloon, as shown in FIGS. 4 to 7. The check valve has an openable closed end resembling the bill of a water mole so that liquid medicine can flow into the balloon assembly but is inhibited from leaking therefrom. Any check valve such as that of the bevel type, flap type, poppet type or ball type can be substituted for the duckbill type. The check valve can be made of a fluoride resin, nylon, polyolefin, polyvinyl chloride, polycarbonate, a silicone resin or the like. The fixed disc 17 supporting the basal end of the check valve has a central opening for flow of the liquid medicine.

In the embodiment shown in FIGS. 4 to 7, the seal 18 is an elastic O-ring fitted in an annular groove formed between the fixed disc 17 and the lockable adapter 7. The O-ring 18 has an inner diameter equal to or slightly smaller than the outer diameter of a junction pipe so that a liquid-tight connection is ensured between the mouth 16 and a junction pipe inserted therein. The lockable adapter 7 is a Luer-tapered cylindrical member, and has an outer screw thread 21 on which a proximal portion of the delivery assembly 'b' can be fastened.

Figure 5:
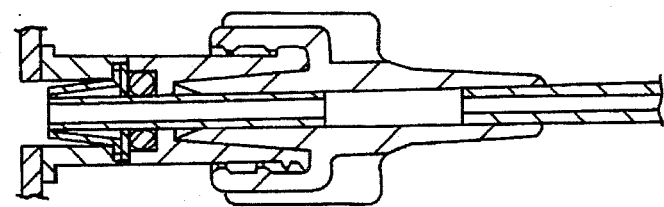
FIG. 5 is a cross-section corresponding to FIG. 4 and showing the adapter engaged with the connector.

The delivery assembly 'b' comprises a proximal connector 12, flow regulator 10, tubing 11 and distal connector 19. The proximal connector 12 is engageable with the lockable adapter 7, and the flow regulator 10 is capable of adjusting the flow rate of the liquid medicine flowing through the tubing 11. A junction pipe 13 protrudes from the proximal connector in a direction opposite to that of the tubing, and is of such a length that it can open the check valve 5 and come into fluid communication with the interior of the balloon assembly. The junction pipe 13 secured to the inner periphery of the connector 12 may be made of a plastic such as polycarbonate, polyvinyl chloride, polyolefin or the like, or a metal such as a stainless steel. The length 'l' of the junction pipe 13 is designed such that it can forcibly open the check valve 5 of the duckbill type when the connector 12 is fastened on to the lockable adapter 7 in a manner as shown in FIG. 5. Because of this feature, an injection needle is not required to discharge the liquid medicine out of the balloon assembly through the forcibly opened check valve 5. A female thread 22 formed in the proximal connector 12 can tightly engage with the male thread 21 of the adapter 7, thereby enabling a liquid-tight connection of the assemblies 'a' and 'b'. Any other mechanism can be employed in place of such a thread connection. Although one mouth 16 is utilized to charge and discharge the liquid medicine in the described embodiment, two mouths can be formed for these purposes. For example, the charging of medicine can be accomplished through the mouth 16, while discharging can be accomplished through a portion of the cylindrical frame adjacent to the hydrophobic filter 4 diametrically opposite the mouth 16.

The flow regulator 10 can be selected from those proposed by the present inventors in Japanese Unexamined Patent Publication Nos. Hei. 1-135356 and 2-11160 incorporated herein by reference. In detail, the regulator can be: (i) a pipe having a closed downstream end and having at least one small orifice; (ii) a perforated pipe such as a porous glass tube; or (iii) a stainless steel or plastic pipe of a small diameter. The flow regulator 10 can be disposed behind the proximal end of the tubing 11 (for example in the proximal connector 12), or between the proximal and distal connectors 12 and 19.

The tubing 11 can be made of soft polyvinyl chloride, polypropylene, polyester or the like. A venous needle or a PSV set is connected to the Luer-tapered connector 19 fixed to the distal end of the tubing 11. A proper check valve (not shown) can be installed in the distal connector 19 so as to prevent backflow of the medicine, against a venous pressure.

Figure 8:
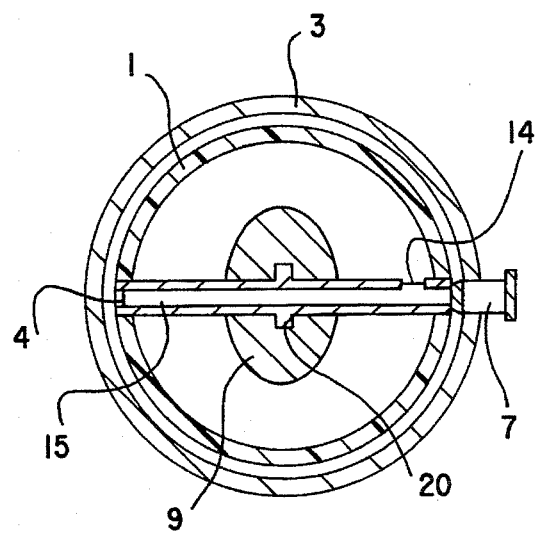
FIG. 8 is a cross-section of an apparatus of the present invention provided in a second embodiment, with its balloon filled with a liquid medicine.

FIG. 8 illustrates a balloon assembly provided in a second embodiment, also for use in a liquid medicine dosing apparatus. A central hollow shaft 15 extends through and axially of the cylindrical frame 2, and a dome-shaped volume adjuster 9 is secured to the shaft and coaxially of the frame. The volume adjuster 9, which regulates the quantity of medicine filled in the balloon to an appropriate volume, is fixed to threaded lugs 20 formed integral with a central portion of the shaft 15. Shaft 15 is a tubular member that has formed in its peripheral wall at least one opening 14 for receiving and delivering liquid medicine. Mouth 16 and hydrophobic filter 4 are attached to opposite ends of the shaft 15. Medicine which enters the balloon through the opening 14 will inflate the balloon, which will then tend to shrink to inject the medicine into a patient, through the delivery assembly 'b'.

Figure 6:
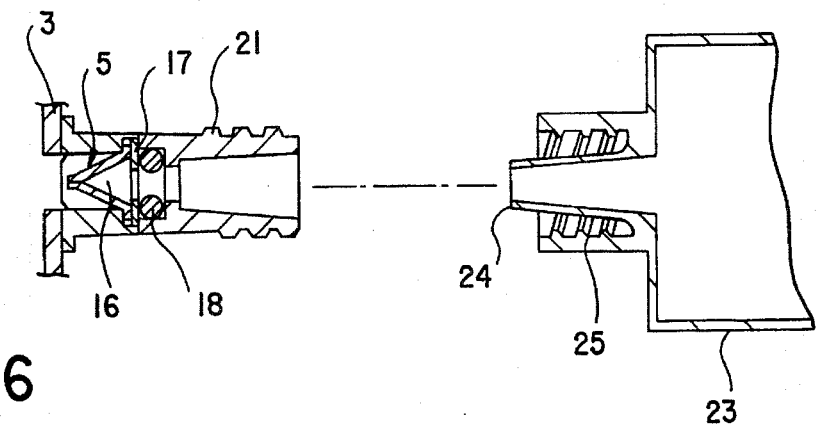
FIG. 6 is a cross-section of a distal end of a syringe which is ready to engage the balloon so as to transfer thereto a liquid medicine.
Figure 7:
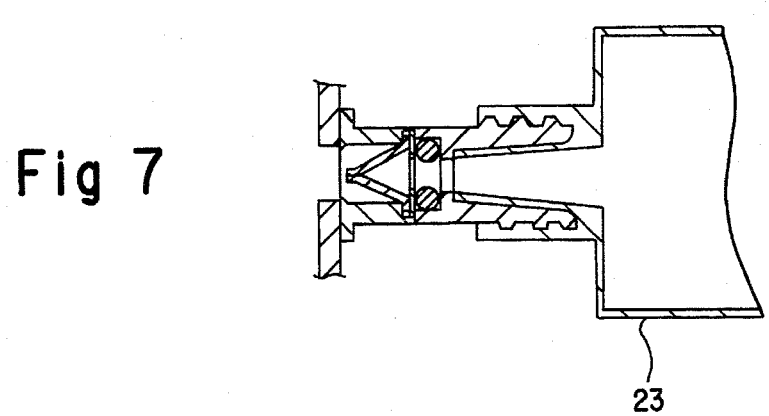
FIG. 7 is a cross-section corresponding to FIG. 6 and showing the syringe transferring its contents to the balloon.

In the use of the apparatus provided in the first or second embodiment, the filling of the balloon with the liquid medicine will be done using a syringe 23, in a manner shown in FIGS. 6 and 7. In detail, a needle holder 24 of the syringe will be pressed in to the Luer-tapered lockable adapter 7, and then the former's thread 25 will be screwed onto the latter's thread 21 such that a proximal end of the needle holder 24 will terminate short of a distal opening of the check valve 5. The needle holder 24 is of a diameter much greater than that of conventional injection needles, so that the loading of said medicine can be done easily and finished in a short time.

As liquid medicine is forced into the balloon assembly, the balloon members 1 and 1' will expand in opposite directions towards and guided along the housing 3, with air being purged through the hydrophobic filter 4. After the balloon has been filled with a predetermined amount of the medicine, the syringe will be removed from the lockable adapter 7. Subsequently, the proximal connector 12 of the delivery assembly 'b' will be coupled with the adapter so that the junction pipe 13 forcibly opens the check valve 5 and comes into fluid communication with the interior of balloon assembly 'a'. The distal end of the tubing will then be connected by distal connector 19 to a PSV set or the like for dosing the medicine to a patient. Although FIGS. 4 to 7 have been used to illustrate the mutual connection of the assemblies 'a' and 'b' any other mode of connection is available in the present invention. A pricking needle may be used with a cock for the mutual connection of the assemblies, or a three-way cock may be used with assemblies which are previously connected one to another so as to charge and discharge the liquid medicine, as disclosed in Japanese Unexamined Patent Publication Hei. 1-135360. Alternatively a Y-shaped pipe may be used for the same purpose as illustrated in Japanese Unexamined Patent Publication Hei. 2-11160. The balloon members proposed herein may also be employed in any of the liquid medicine dosing apparatuses disclosed in: Japanese Patent Publication Hei. 3-55142, Domestic Re-Publication Hei. 1-501451, and Unexamined Patent Publications Hei. 2-11160 and 3-170163.

Figure 9:
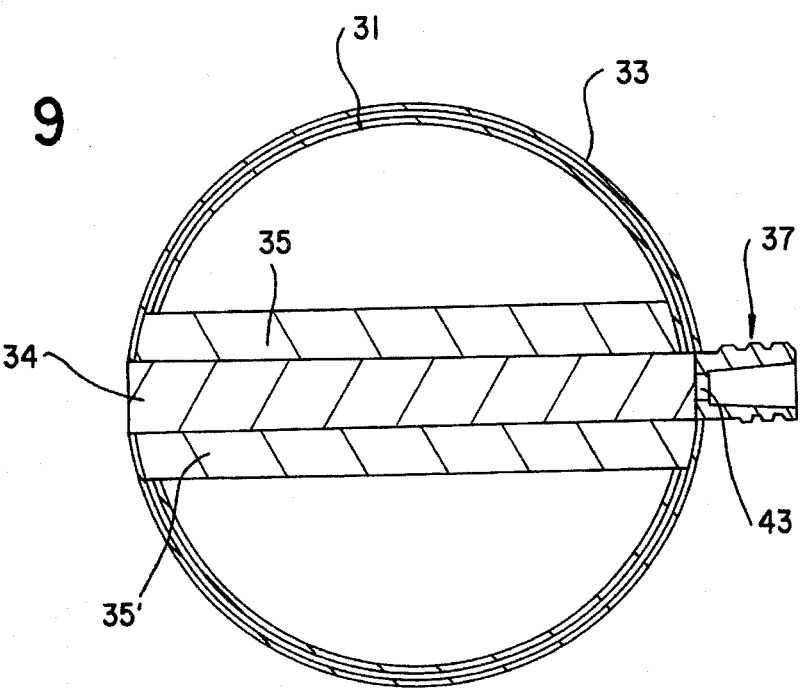
FIG. 9 is a cross-section of an apparatus of the present invention in a third embodiment, its balloon filled with a medicine.
Figure 10:
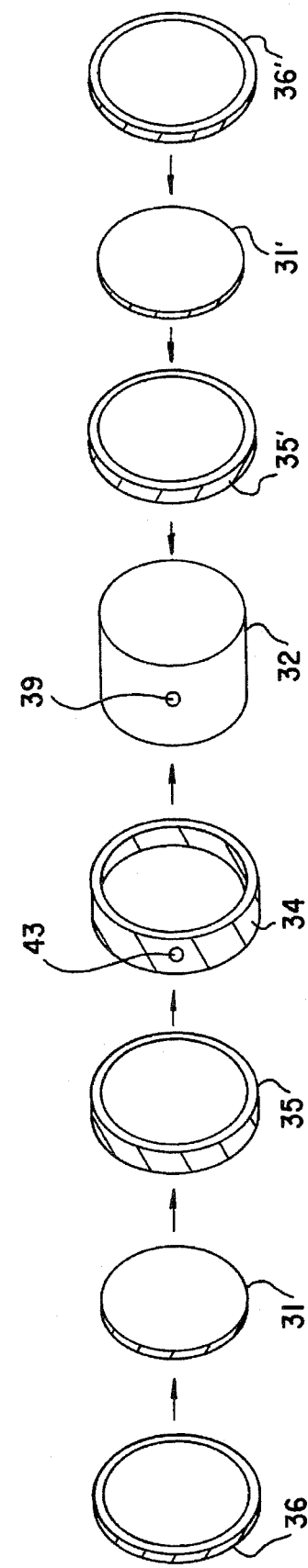
FIG. 10 is a perspective view of a process for manufacturing the balloon shown in FIG. 9.

In a third embodiment shown in FIGS. 9 and 10, sheet-shaped balloon members 31 and 31' secured to the opposite ends of a short cylindrical frame 32 (see FIG. 10) by means of fasteners 36 and 36' are inflated with the liquid medicine, so as to assume the shape of a sphere as a whole. The balloon members need not be of any specified size of thickness in the invention, since they should vary depending on the quantity of dosed medicine and the rate of dosing the same to a patient.

An opening 39 (see FIG. 10) is formed in the peripheral wall of cylindrical frame 32. The medicine can flow through the opening and a mouth 43 of a rotary collar 34 (detailed below) while the mouth 43 of the rotary collar 34 is kept in alignment with the opening. Semi-spherical housings 33 are fixed to the short cylindrical frame 32 and outside the balloon members. Stationary collars 35 and 35' (see FIG. 10) can have male threads engaging with female threads formed along inner peripheries of the housings. The housings will protect the balloon members 31 and 31' from puncture and breakage due to collision with an acute object, and will also inhibit liquid medicine from ejecting through a pin hole possibly present in said members. An opening (not shown) for ventilation is formed through a proper portion of the housing 33. Air and gases can pass through a hydrophobic filter attached to this opening, but liquids are prevented from doing so.

FIG. 10 illustrates a process of manufacturing the balloon assembly 'a' in the third embodiment, wherein the rotary collar 34 is first fitted on cylindrical frame 32 having opening 39. Rotary collar 34 having aperture 43 is rotatable around the frame so that the aperture coincides with opening 39 to thereby allow the liquid medicine to flow inwardly or outwardly through the opening 39 and the aperture 43. Then, the stationary collars 35 and 35' are fitted on and secured to the frame 32, close to the respective sides of the stationary collar (see FIG. 9). Subsequently, the balloon members 31 and 31' are placed on the opposite ends of the cylindrical frame 32 of the stationary collars 35 and 35' fixed thereon, such that annular grooves formed in the frame or collars are covered with the balloon members. Finally, O-ring-shaped fasteners 36 and 36' force circular edges of the balloon members into the annular grooves, thus fixing said members on the frame or stationary collars.

Figure 11:
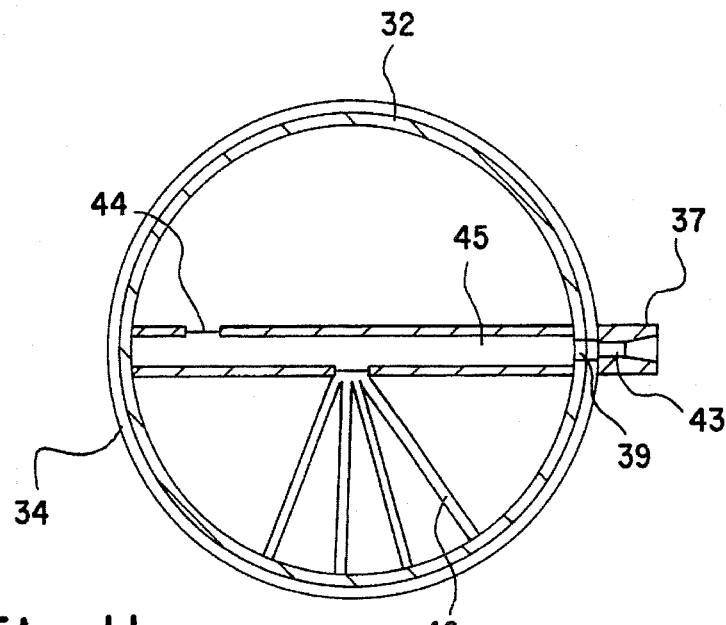
FIG. 11 is a cross-section of an apparatus of the present invention in a fourth embodiment, its balloon filled with a medicine.

FIG. 11 illustrates a balloon assembly 'a' provided in a fourth embodiment, also for incorporation in a liquid medicine dosing apparatus. A central hollow shaft 45 extends through and axially of the cylindrical frame 32, and at least one tubular passageway 42 extends radially from the center of hollow shaft 45 to the inner periphery of the frame 32. Additional mouths which are formed in the narrow peripheral wall of the frame 32 communicate with respective outer openings of the tubular passageways 42. Flow regulators for different flow rates of a liquid medicine are installed in the passageways so that a rotary collar 34 is rotated to select any desired flow rate. Therefore, any additional flow regulator corresponding to regulator 10 secured in the delivery assembly 'b' in the first embodiment can be eliminated in the fourth embodiment. For use, a liquid medicine is fed to the balloon assembly, through lockable adapter 37 communicating with an aperture 43 (of the rotary collar 34, see FIG. 10) and mouth 39 (of the cylindrical frame 32). The medicine flowing into the hollow shaft 45 flows out of the hollow shaft through an opening 44 formed therein, so as to inflate the balloon members 31 and 31' (see FIG. 10). Then, any desired one of the additional mouths of the tubular passageways 42 is aligned with the aperture 43 formed in the rotary collar 34, whereby the shrinking balloon members will squeeze and force the liquid medicine into a patient via delivery assembly 'b'. A single opening 44 is formed in the peripheral wall of the hollow shaft 45 shown in FIG. 11 but there can be at least two openings.

Figure 12:
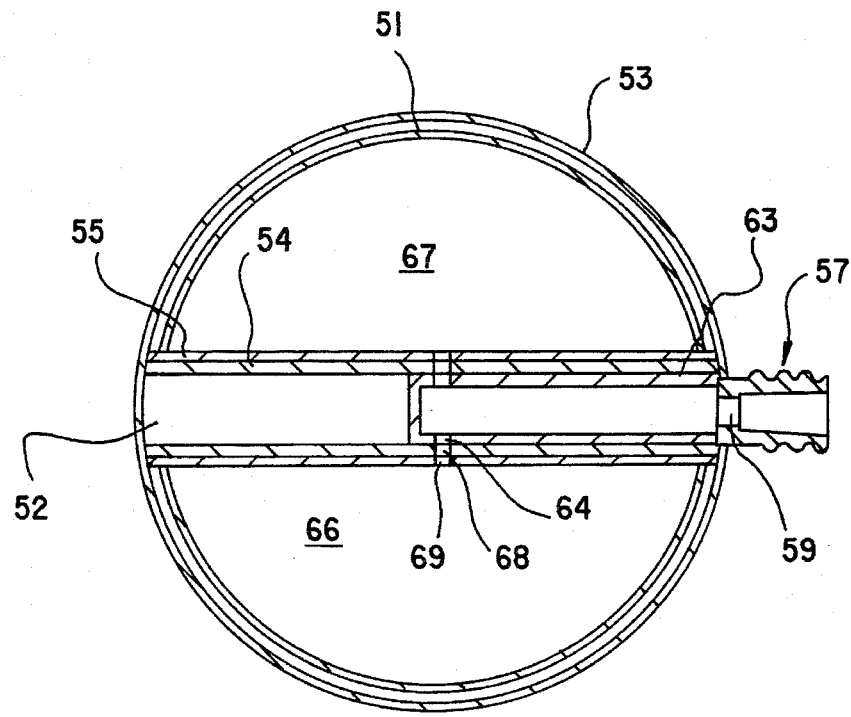
FIG. 12 is a cross-section of an apparatus of the present invention in a fifth embodiment, its balloon filled with a medicine.

FIG. 12 illustrates a fifth embodiment, wherein also a balloon assembly comprises sheet-shaped balloon members 51 fixed by fasteners to both sides of a short cylindrical frame 52. The balloon assembly composed of members 51 will substantially assume the shape of a sphere as a whole if and when inflated with medicine. The balloon members need not be of any specified size or thickness in the invention, since they should vary depending on the quantity of dosed medicine and the rate of dosing same to a patient. A first chamber 66 and a second chamber 67 are defined in the balloon assembly in this embodiment, and the first chamber 66 is of a capacity large enough to accommodate the liquid medicine fraction held in the second one 67 in addition to that held in the first one 66.

A mouth 59 for the liquid medicine is formed in the narrow peripheral wall of cylindrical frame 52. A fixed hollow shaft 55 extends from the mouth 59, through the frame's center and to a wall portion located opposite the mouth. Two openings 68 formed in the shaft 55 are located adjacent to a center thereof so as to communicate with the first and second chambers 66 and 67, respectively. A partitioning sheet 54 in close contact with the outer periphery of the shaft 55 divides the interior into two chambers and has round apertures 69 in alignment with the openings 68. A cylindrical rotor 63 is held rotatably in the fixed hollow shaft 55, in a sliding contact therewith. Three mouths 64 (hereinafter referred to as 'three-way cock') formed in the peripheral wall of rotor 63 assume three extremities of the letter "T", thus cooperating with a relatively spacious interior of the rotor to provide a three-way cock for liquid medicine. Thus, depending on the angle of said rotor 63 relative to the outer fixed shaft 55, liquid in the second chamber 67 can move in to the first chamber. Alternatively, a first liquid medicine can flow in to the first chamber 66, or a second liquid medicine can flow into the second chamber 67, or a mixture of the first and second liquids can flow outwardly through the mouth 59. The rotor 63 can have a thinner interior such that three paths of a T-shape are formed leading to the openings 69, to bear a closer resemblance to a usual three-way cock.

Figure 4:
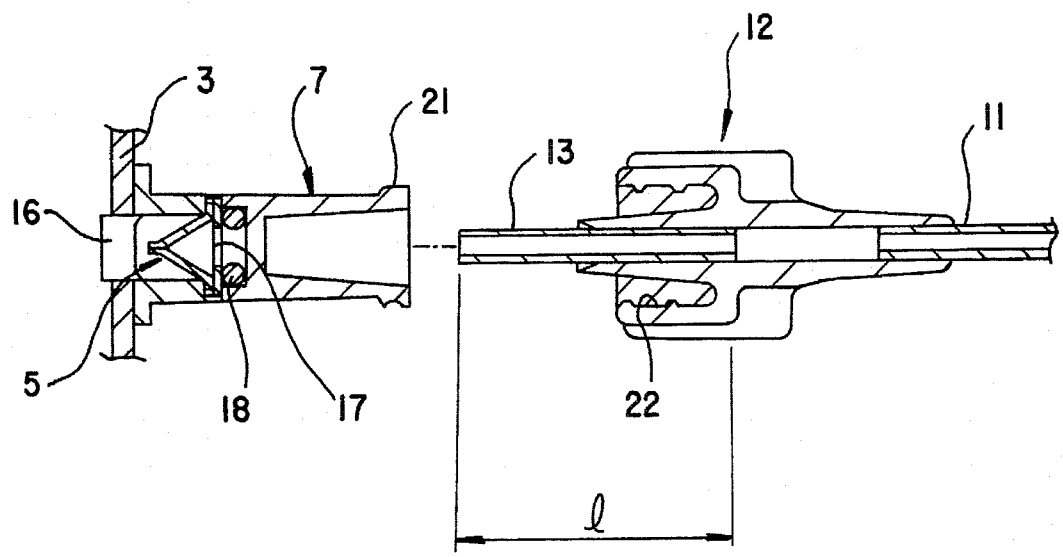
FIG. 4 is an enlarged cross-section of a lockable adapter shown in FIG. 3 and engageable with a connector of the delivery assembly.

In operation, the three-way cock 64 formed in the rotor 63 is set at a first position so that the first chamber 66 can receive an amount of a first liquid medicine. Subsequently, a syringe 23 is engaged with the lockable adapter 57, in a manner as shown in FIGS. 6 and 7. In detail, needle holder 24 of syringe 23 will be placed in the Luer-tapered recess of the adapter 57, before fastening the thread of the syringe onto that of the adapter. Balloon members 51 will continue to expand due to the liquid medicine supplied in this manner, until the syringe is removed from the adapter when the balloon assembly 'a' has been loaded with a predetermined amount of the medicine. Next, the three-way cock 64 is set at a second position so that second chamber 67 can likewise receive a second liquid medicine from another syringe 23. Thereafter, the cock will be turned to a third position where the first chamber 66 communicates with the second chamber 67, in order to cause the content of second chamber to transfer into the first one. Finally, the second chamber will be closed with the three-way cock 64, before the delivery assembly 'b' is connected to the balloon assembly 'a' by placing the proximal connector 12 in the lockable adapter 57 and tightening the thread 22 of the connector onto the thread 21 of the adapter as illustrated in FIG. 4 and 5. The three-way cock 64 is further rotated to cause the second chamber 67 to communicate with the adapter 57, a PSV set or the like is attached to the distal connector 19, and the internal air is purged before dosing the mixture of liquid medicines. It will be understood that a powdery medicine can be mixed with a liquid medicine within the balloon assembly of this embodiment, before being dosed to a patient.

EXAMPLE 1

A composite elastic sheet was prepared by lamination of a BARIALON polyethylene sheet manufactured by Asahi Chemical Industry Co. and having a density of 0.91 g/cm$^3$ and thickness of 150 μm and a scoured and finished rubber sheet having a thickness of 100 μm. Circular pieces having a diameter of 60 mm were cut from the composite sheet. The natural rubber sheet was previously refined by extracting the additives from a raw vulcanized rubber sheet and subsequently impregnating the sheet with an antioxidant. In detail, a raw rubber sheet (made by Komine Rubber Co., Ltd.) was subjected to an extraction process for 3 hours in a Soxhlet extractor using a mixed solvent composed of 1 part by volume of acetone and 2 parts by volume of hexane. The impregnation of the antioxidant was done by dipping the refined rubber sheet in a 0.01 g/ml solution of BHT (viz. 1,3,5-trimethyl-2,4,6-tris(3,5-di-t-butyl-4-hydroxybenzyl-)benzene) dissolved in the acetone-hexane mixed solvent, for 24 hours at 25° C.

Figure 13:
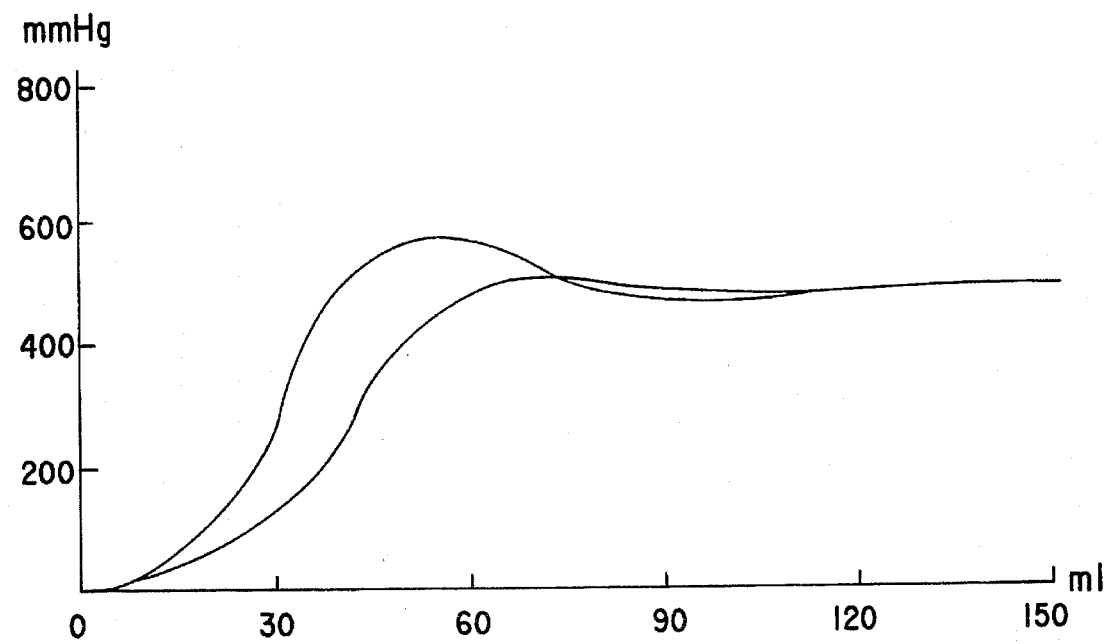
FIG. 13 is a graph showing the relationship observed between the quantity and the pressure of liquid medicine present in the balloon shown in FIG. 1.

The scoured and impregnated rubber sheet was then washed with ethanol and dried at 25° C. for 12 hours, and bonded to the polyethylene sheet to produce the laminate mentioned above. The circular pieces cut from this laminate were attached to opposite sides of a cylindrical frame, in a manner shown in FIG. 2, with the polyethylene layer positioned inside the rubber layer. A balloon assembly 'a' prepared in this manner as shown in FIG. 3 was then filled with 150 ml of water, before being connected to a delivery assembly 'b'. Performance of this balloon assembly was tested at a constant flow rate of 100 ml per hour of the water effluent from said assembly, by measuring and plotting the pressure of water against the volume thereof remaining in the balloon and decreasing in the course of time. The result obtained is shown in FIG. 13, which indicates that an almost constant internal pressure continues to urge the water to flow at a constant rate out of the balloon insofar as the volume of the remaining water is 70 ml or more.

EXAMPLE 2

Figure 14:
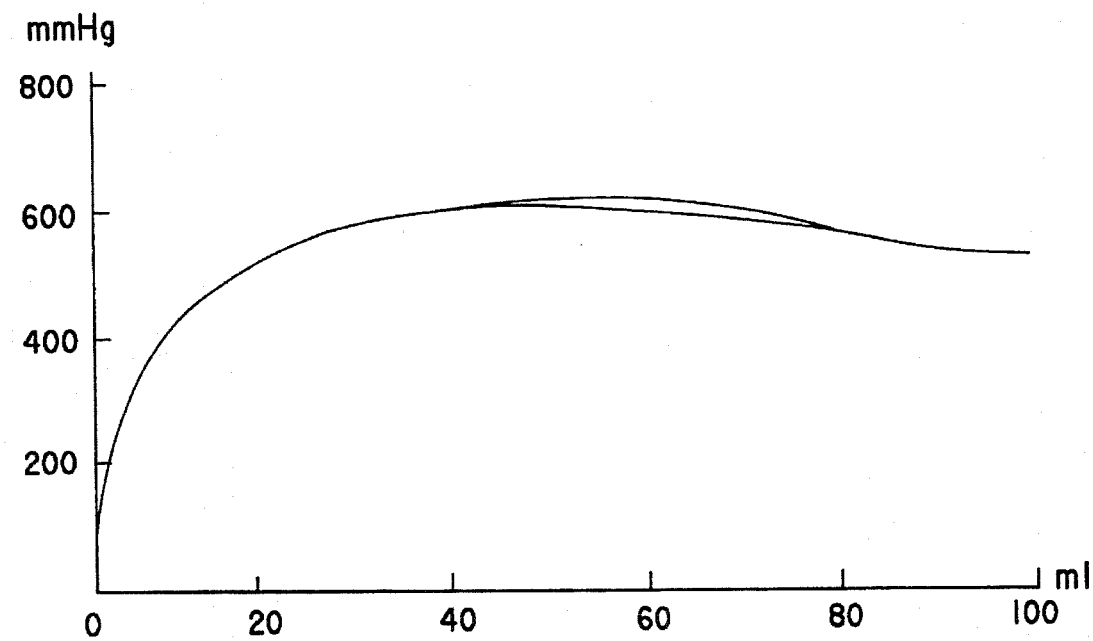
FIG. 14 is a graph similar to that shown in FIG. 13, but for the balloon shown in FIG. 8.

The balloon assembly in EXAMPLE 1 was modified by fixing in the cylindrical frame a hollow shaft to extend therethrough and across the center thereof, and attaching to a central portion of the shaft a dome-shaped volume adjuster having a volume of about 30 cm$^3$, as illustrated in FIG. 8. This balloon assembly was also filled with 100 ml of water and was connected to the delivery assembly. Performance of this balloon assembly was tested similarly at a constant flow rate of 100 ml per hour of the water flowing out of or into said assembly, by plotting the pressure of water against the volume thereof remaining in the balloon. The result obtained is shown in FIG. 14 which indicates that the internal pressure remains more constant as compared with EXAMPLE 1, whether the water is flowing into or out of the balloon.

Reference 1

A length of polyethylene tube (having an inner diameter of 4.3 mm, an outer diameter of 4.6 mm and a length of 60 mm) having one end closed was folded in the direction of its axis. An end portion including the closed end was dipped in a silicone oil bath so that the outer surface of said portion was coated with the silicone oil. On the other hand, a length of vulcanized natural rubber tube (made by Komine Rubber Co., Ltd.) was subjected to a scouring process similar to that employed in EXAMPLE 1. The natural rubber tube thus refined and having one end closed had an inner diameter of 5.0 mm, an outer diameter of 7.0 mm and a length of 95 mm. The polyethylene tube having its end coated with silicone oil was then inserted into the refined natural rubber tube, and the silicone oil was further poured in between the tubes, before their open ends were adjoined one to another and a compressed air was applied into the polyethylene tube to expand together with the rubber tube. The excessive portion including the open end of the rubber tube was cut off so that the two tubes were of the same length, and the air remaining in the polyethylene tube was purged to give a balloon of the prior art type. The silicone oil formed a layer evenly spread throughout the interface between the two tubes of this balloon. The average thickness of the silicone oil layer was about 0.09 µm. This balloon was used to form a balloon assembly for dosing a liquid medicine, as disclosed for example in Japanese Unexamined Patent Publication Hei. 4-96761. The balloon was then filled and inflated with 100 ml of water, using the syringe. No void was found between the tubes, thus demonstrating a close contact of the outer periphery of the polyethylene tube with the inner periphery of the rubber tube. The connector of delivery assembly 'b' was then engaged with the lockable adapter of the balloon assembly, to discharge the water therefrom through the tubing in a manner shown in FIG. 1.

Figure 16:
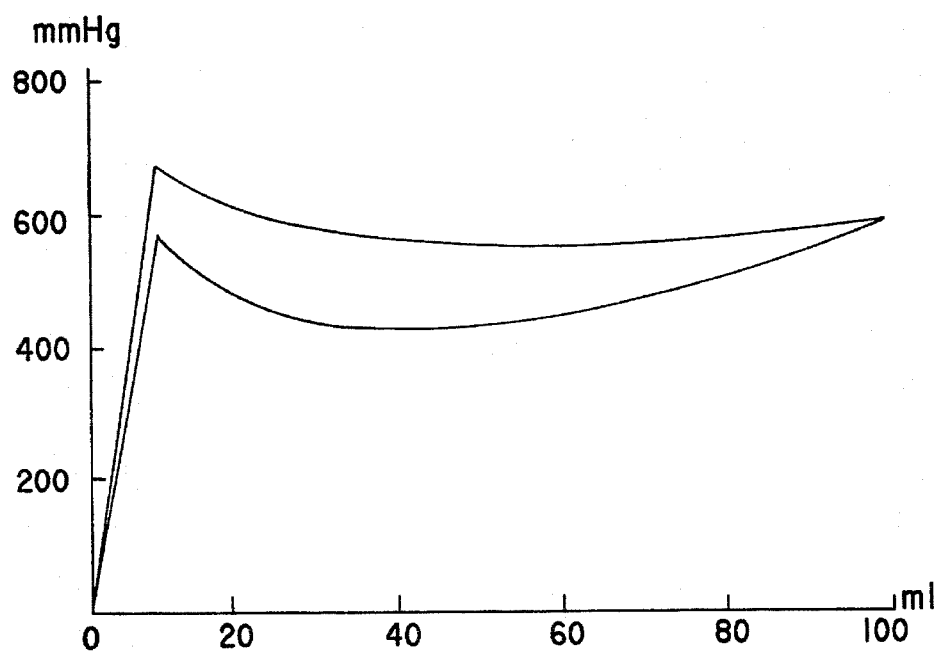
FIG. 16 is a similar graph for prior art balloons.

Performance of this balloon assembly for reference was tested similarly at a constant flow rate of 100 ml per hour of the water effluent out of the assembly, by plotting the pressure of water against the volume thereof remaining in balloon. As shown in FIG. 16, not only was a significant difference found in the internal pressure between the processes of charging and discharging of the water, but also no constant pressure was observed whether the water was flowing into or out of the balloon.

EXAMPLE 3

A composite elastic sheet was prepared by lamination of a polyethylene sheet having a thickness of 150 µm and a scoured and finished rubber sheet having a thickness of 100 µm. Circular pieces having a diameter of 60 mm were cut from the composite sheet. The natural rubber sheet was previously refined by extracting the additives from a raw vulcanized rubber sheet and subsequently impregnating the sheet with an antioxidant. In detail, a raw rubber sheet (made by Komine Rubber Co., Ltd.) was subjected to an extraction process for 3 hours in a Soxhlet extractor using a mixed solvent composed of 1 part by volume of acetone and 2 parts by volume of hexane. The impregnation of the antioxidant was done by dipping the refined rubber sheet in a 0.01 g/ml solution of BHT (viz. 1,3,5-trimethyl-2,4,6-tris (3,5-di-t-butyl-4-hydroxybenzyl)benzene) dissolved in the acetone-hexane mixed solvent, for 24 hours at 25° C.

Figure 15:
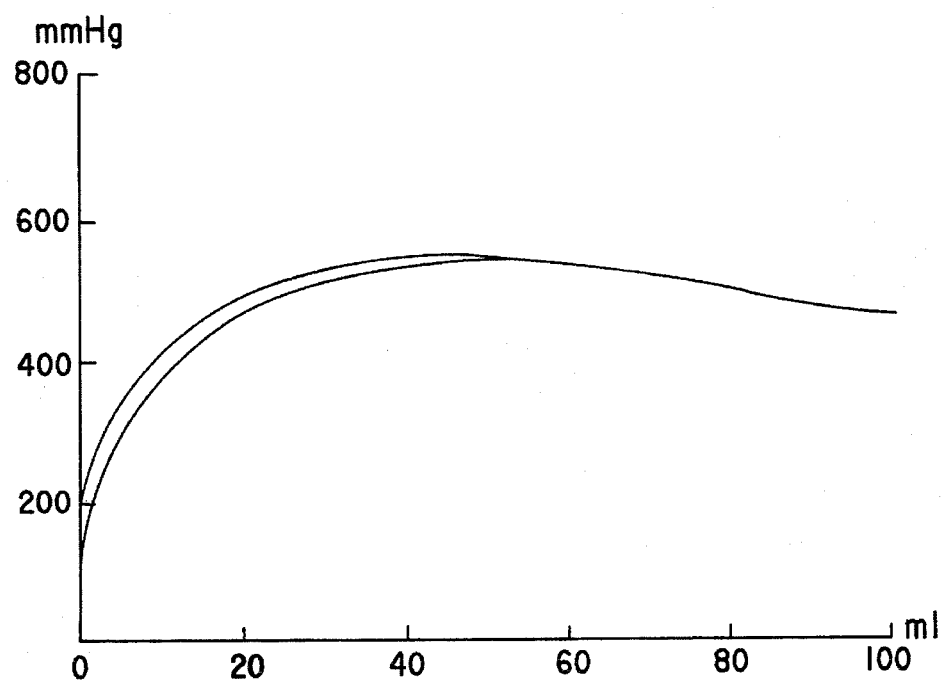
FIG. 15 is a graph similar to that shown in FIG. 13, but for the balloon shown in FIG. 9.

The scoured and impregnated rubber sheet was then washed with ethanol and dried at 25° C. for 12 hours, and bonded to the polyethylene sheet to produce the laminate mentioned above. The circular pieces cut from this laminate were attached to opposite sides of a cylindrical frame, in a manner as shown in FIG. 10, with the polyethylene layer positioned inside the rubber layer. A balloon assembly 'a' prepared in this manner as shown in FIG. 9 was then filled with 100 ml of water, before being connected to a delivery assembly 'b'. Performance of this balloon assembly was tested at a constant flow rate of 100 ml per hour of water effluent from said assembly, by measuring and plotting the pressure of the water against the volume thereof remaining in the balloon and decreasing in the course of time. The result obtained is shown in FIG. 15, indicating that an almost constant internal pressure continues to urge the water to flow at the constant rate out of the balloon insofar as the volume of remaining water is 40 ml or more.

EXAMPLE 4

A composite elastic sheet was prepared by lamination of a polyethylene sheet having a thickness of 150 µm and a scoured and finished rubber sheet having a thickness of 100 µm. A circular piece having a diameter of 60 mm and another circular piece having a diameter of 45 mm were cut from the composite sheet. The natural rubber sheet was previously refined by extracting the additives from a raw vulcanized rubber sheet and subsequently impregnating the sheet with an antioxidant. In detail, a raw rubber sheet (made by Komine Rubber Co., Ltd.) was subjected to an extraction process for 3 hours in a Soxhlet extractor using a mixed solvent composed of 1 part by volume of acetone and 2 parts by volume of hexane. The impregnation of the antioxidant was done by dipping the refined rubber sheet in a 0.01 g/ml solution of BHT (viz. 1,3,5-trimethyl-2,4,6-tris (3,5-di-t-butyl-4-hydroxybenzyl)benzene) dissolved in the acetone-hexane mixed solvent, for 24 hours at 25° C. The scoured and impregnated rubber sheet was then washed with ethanol and dried at 25° C. for 12 hours, and bonded to the polyethylene sheet to produce the laminate mentioned above. The circular pieces having the diameter of 60 mm and 45 mm cut from this laminate were attached to opposite sides of a cylindrical frame, respectively, with the polyethylene layer positioned inside the rubber layer. A balloon assembly was prepared in this manner as shown in FIG. 12, and a second chamber defined with the smaller circular sheet of diameter of 45 mm was then filled and inflated with 15 ml of an amino acid solution. The internal pressure of the second chamber was 580 mmHg. After the three-way cock of the assembly was rotated a desired angle, a first chamber defined with the larger circular sheet of diameter of 60 mm was also filled and inflated with 33 ml of a glucose solution. The internal pressure of the first chamber was 440 mmHg. The three-way cock was rotated again an angle to cause the chambers to communicate with each other so that the amino acid solution was transferred from the second chamber to the first one. The three-way cock was rotated a further angle to close the first chamber and to blend the solutions with each other before connecting the balloon assembly to a delivery assembly 'b' so as to test the performance of the assembly at a constant flow rate of 100 ml per hour of the mixed solution effluent from the balloon assembly.

The flat sheets constituting the balloon of the apparatus of the present invention are of an even thickness over their whole area, even after being inflated with a liquid medicine. Therefore, the pressure as well as the flow rate of the liquid medicine effluent from the balloon scarcely varies at the opening thereof over the course of time. A flow regulator which receives such a stable flow of the medicine can thus dose it to a patient at a constant flow rate. If a dome-shaped volume adjuster fixed to a central portion of the cylindrical frame is enclosed in the balloon, then no noticeable fluctuation will take place in pressure at the inlet of a flow regulator, thus ensuring a more stable continuous dosing of the liquid medicine.

What is claimed is:

1. An apparatus for dosing a liquid medicine, the apparatus including a balloon assembly and a delivery assembly connected thereto, the balloon assembly comprising:

flat and flexible circular sheet-shaped balloon members inflatable to define therebetween an inside space for accommodating an amount of a liquid medicine in a pressurized state;

a housing for enclosing the balloon members in an inflated state thereof; and a short cylindrical frame between the balloon members and having a narrow peripheral wall in which a primary mouth is formed which is directly or indirectly in fluid communication with the space inside the frame, the primary mouth capable of fluid communicating with the delivery assembly, and the delivery assembly extending outwardly from the primary mouth to discharge the liquid medicine out of the balloon assembly, wherein edges of the balloon members are secured to opposite side rims of the cylindrical frame so as to assume a drum shape.

2. An apparatus as defined in claim 1, wherein the delivery assembly comprises a flow regulator.

3. An apparatus as defined in claim 1, wherein the balloon assembly further comprises a means for adjusting the volume within the cylindrical frame, and between the balloon members.

4. An apparatus as defined in claim 1, further comprising a rotary collar fitted on the cylindrical frame and having a mouth that is capable of fluid communicating with the primary mouth.

5. An apparatus as defined in claim 4, further comprising a hollow shaft located inside the rotary collar, a liquid charging passageway and at least one liquid discharge passageway, each said passageway extending from the hollow shaft to the cylindrical frame, wherein a liquid charging opening and a liquid discharge mouth are formed in a peripheral wall of the hollow shaft.

6. An apparatus as defined in claim 5, further comprising at least one flow regulator located in said at least one discharge passageway.

7. An apparatus as defined in claim 1, further comprising a partitioning sheet located between the sheet-shaped balloon members so that the inside space of the balloon assembly is divided into two chambers capable of fluid communicating with each other.

* * * * *